United States Patent
Noderer et al.

(10) Patent No.: US 9,775,952 B2
(45) Date of Patent: Oct. 3, 2017

(54) DRUG DELIVERY DEVICE AND METHOD FOR ASSEMBLING A DRUG DELIVERY DEVICE

(75) Inventors: Michael Noderer, Frankfurt am Main (DE); Timothy Giles Claughton, Cheshire (GB); Warren Terry, Warwickshire (GB); Robert Veasey, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 947 days.

(21) Appl. No.: 13/878,465

(22) PCT Filed: Oct. 25, 2011

(86) PCT No.: PCT/EP2011/068603
§ 371 (c)(1),
(2), (4) Date: Apr. 9, 2013

(87) PCT Pub. No.: WO2012/055845
PCT Pub. Date: May 3, 2012

(65) Prior Publication Data
US 2013/0204183 A1 Aug. 8, 2013

(30) Foreign Application Priority Data
Oct. 25, 2010 (EP) .................................... 10188657

(51) Int. Cl.
*A61M 5/315* (2006.01)
*A61M 5/31* (2006.01)
(Continued)

(52) U.S. Cl.
CPC .......... *A61M 5/31533* (2013.01); *A61M 5/31* (2013.01); *A61M 5/3135* (2013.01);
(Continued)

(58) Field of Classification Search
CPC .. A61M 2005/2026; A61M 2005/2086; A61M 2005/2073; A61M 2005/2418;
(Continued)

(56) References Cited

U.S. PATENT DOCUMENTS 5,295,976 A * 3/1994 Harris ............... A61M 5/31551
604/208
6,193,698 B1 * 2/2001 Kirchhofer ....... A61M 5/31551
604/207

(Continued)

FOREIGN PATENT DOCUMENTS

EP 1923093 5/2008
WO WO 2007/138313 A1 * 12/2007 ...... A61M 2005/208
(Continued)

OTHER PUBLICATIONS

International Search Report for Int. App. No. PCT/EP2011/068603, completed Dec. 5, 2011.

*Primary Examiner* — Imani Hayman
*Assistant Examiner* — James D Ponton
(74) *Attorney, Agent, or Firm* — McDonnell Boehnen Hulbert & Berghoff LLP

(57) ABSTRACT

A drug delivery device comprises a first component and a second component, wherein a substance is provided on at least one of the first component and the second component. An inner friction of the substance is great enough to stabilize at least one of the orientation and the position of the first component and the second component with respect to one another. The inner friction of the substance is small enough to allow relative movement of the first component and the second component necessary for the intended operation of the device. Furthermore, a method for assembling a drug delivery device is provided.

12 Claims, 4 Drawing Sheets

(51) Int. Cl.
*A61M 5/24* (2006.01)
*A61M 5/30* (2006.01)

(52) U.S. Cl.
CPC .............. *A61M 5/3146* (2013.01); *A61M 5/30* (2013.01); *A61M 5/31515* (2013.01); *A61M 5/31568* (2013.01); *A61M 2005/2407* (2013.01); *A61M 2005/2488* (2013.01); *A61M 2005/3125* (2013.01); *A61M 2005/3126* (2013.01); *A61M 2005/3151* (2013.01); *A61M 2205/0222* (2013.01); *A61M 2207/00* (2013.01)

(58) Field of Classification Search
CPC .. A61M 2005/3125; A61M 2025/1062; A61M 2025/1088; A61M 5/3146; A61M 5/315; A61M 5/31501; A61M 5/31525; A61M 5/3155; A61M 5/31551; A61M 5/31553; A61M 5/31555; A61M 5/31556; A61M 5/31563; A61M 5/31568; A61M 5/178; A61M 5/20; A61M 5/31526; A61M 5/31528; A61M 5/315655; A61M 5/31595; A61M 5/31565; A61M 5/31533; A61M 5/31535
See application file for complete search history.

(56) References Cited

U.S. PATENT DOCUMENTS

| | | | |
|---|---|---|---|
| 6,221,046 B1* | 4/2001 | Burroughs | A61M 5/31551 604/153 |
| 2003/0187405 A1 | 10/2003 | Gatti et al. | |
| 2010/0049125 A1* | 2/2010 | James | A61M 5/2033 604/110 |

FOREIGN PATENT DOCUMENTS

| | | |
|---|---|---|
| WO | 2008/015066 | 2/2008 |
| WO | 2009/030975 | 3/2009 |

* cited by examiner

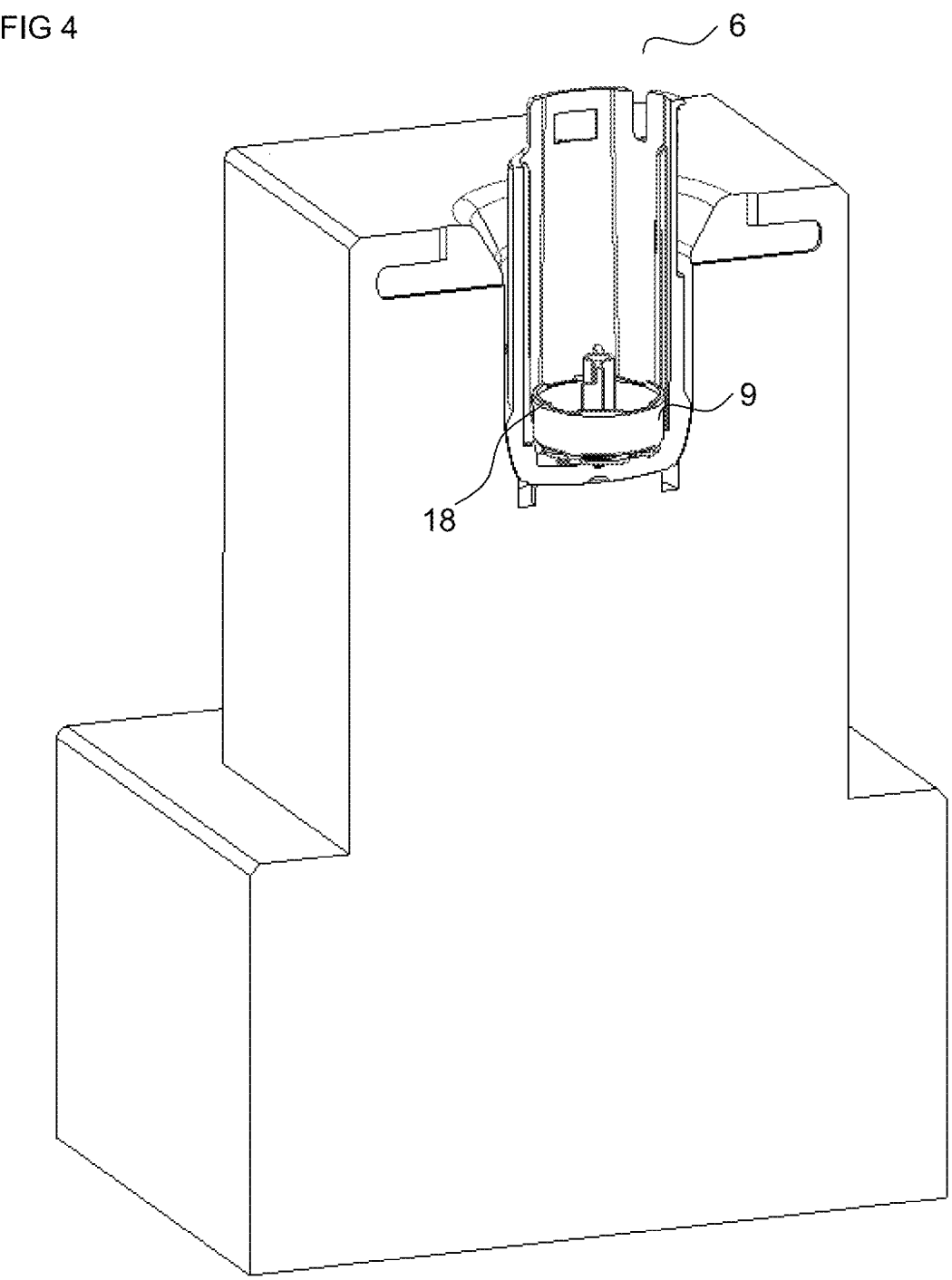

DRUG DELIVERY DEVICE AND METHOD FOR ASSEMBLING A DRUG DELIVERY DEVICE

CROSS REFERENCE TO RELATED APPLICATIONS

The present application is a U.S. National Phase Application pursuant to 35 U.S.C. §371 of International Application No. PCT/EP2011/068603 filed Oct. 25, 2011, which claims priority to European Patent Application No. 10188657.0 filed on Oct. 25, 2010. The entire disclosure contents of these applications are herewith incorporated by reference into the present application.

FIELD OF DISCLOSURE

This disclosure relates to a drug delivery device and to a method for assembling a drug delivery device.

BACKGROUND

In a drug delivery device a bung is, often, provided within a cartridge that contains a drug. The bung is displaced with respect to the cartridge by a piston rod for delivering a dose of the drug. The piston rod may be driven by a drive mechanism of the drug delivery device.

A drug delivery device is described in document EP 1 923 093, for example.

SUMMARY

It is an object of the present disclosure to facilitate provision of an improved drug delivery device, for example a device with high dose accuracy or with increased user safety.

This object may be achieved by the subject-matter of the independent claims. Further features are the subject-matter of the dependent claims.

According to one aspect, a drug delivery device is provided. The drug delivery device comprises a first component. The drug delivery device comprises a second component. A substance is provided on at least one of the first component and the second component. The substance comprises an inner friction. The inner friction is preferably great enough to stabilize the orientation and/or the position of the first component and the second component with respect to one another. The position may comprise at least one of an axial and an angular position of the first component and the second component with respect to one another. The inner friction of the substance is small enough to allow relative axial and/or rotational movement of the first component and the second component necessary for intended operation of the device, e.g. for at least one of setting and dispensing of a dose of a drug.

Relative movement of the first component and the second component may comprise at least one of axial and/or rotational movement of the first component with respect to the second component and axial and/or rotational movement of the second component with respect to the first component.

The substance may pose a threshold of impact counteracting any force acting on the respective component. The threshold has to be overcome in order to initiate relative movement of the first and the second component with respect to one another. The threshold, in particular the inner friction of the substance, may be chosen such that any force arising beyond the intended operation of the device and acting on the respective component, e.g. a force arising from movement possible due to play between the components, is prevented from overcoming the threshold. Thus, unintentional relative movement of the first component and the second component may be prevented. Accordingly, a predetermined position of the first component and the second component with respect to one another may be maintained by means of the substance. Dose accuracy may be increased in this way.

The threshold, in particular the inner friction of the substance, may be chosen such that any force arising from intended operation of the device and acting on the respective component, e.g. a force caused by a drive mechanism of the device, is allowed to overcome the threshold. Thus, intentional relative movement of the first component and the second component for operation of the device may be allowed.

According to an embodiment, the inner friction of the substance is great enough to prevent relative axial and/or rotational movement of the first and second component caused by an outer impact or by a vibration of the device.

The device may, for example, be subject to vibrations, e.g. during transport of the device. Forces arising from said vibrations acting on the first and the second component may be counteracted by means of the substance, in particular due to the inner friction of the substance.

According to an embodiment, the inner friction of the substance is great enough to prevent relative axial and/or rotational movement of the first and the second component arising from a manufacturing tolerance of at least one of the first component and the second component. Additionally or alternatively, the inner friction of the substance may be great enough to prevent relative movement of the first and the second component arising from manufacturing tolerances during assembly of the device.

Said manufacturing tolerances may lead to play between the first component and the second component. The first component and the second component may be prone to relative movement with respect to one another due to said play. However, this may reduce dose accuracy of the device. The inner friction of the substance is preferably great enough to prevent relative movement due to said play.

According to an embodiment, a force applied to at least one of the first and the second component during intended operation of the device is great enough to overcome the inner friction of the substance.

Intended operation of the device may comprise the operation of setting and/or delivering of a dose of a drug from the device, for example. The force applied on at least one of the first and the second component during said operations may be great enough and, accordingly, the inner friction of the substance may be small enough to overcome the inner friction, the first component and the second component thus being moveable with respect to one another. Intended use of the device may be guaranteed in this way.

According to an embodiment, the first component and the second component are part of a drive mechanism of the device. Relative movement of the first component and the second component may be allowed as far as being necessary for operation of the drive mechanism, e.g. for setting and/or delivering of a dose of the drug.

According to an embodiment, an outer shape of the first component and the second component is predetermined by the intended operation of the device, in particular the intended operation of the drive mechanism.

In particular, modification of the first component and the second component, e.g. of their outer shape, may not be necessary to prevent unintentional relative movement of the first component and the second component. In this way, a cost-effective drug delivery device may be achieved.

According to an embodiment, the substance is adhesively coupled to an outer surface, e.g. a bearing surface, of at least one of the first component and the second component.

The respective bearing surface may be adapted and arranged to mechanically cooperate with the bearing surface of the other one of the first component and the second component. Upon mechanical cooperation of the bearing surfaces, relative movement of said components may be prevented by means of the substance applied to, in particular coupled to, the respective bearing surface counteracting a force which tends to initiate relative movement of the first and the second component. The material property of the substance may be chosen such that the substance is coupled to the outer surface of at least one of the first component and the second component in such a way that it is not removed or destroyed upon mechanical cooperation of the first component and the second component, in particular of their bearing surfaces.

According to an embodiment, the substance comprises a viscous fluid. The substance may comprise a grease, for example.

According to an embodiment, the first component comprises a dose button of the device. The dose button may be configured to be actuated by a user for at least one of setting and dispensing a dose of the drug from the device.

According to an embodiment, the second component comprises a dose indicator element of the device. The dose indicator element may be configured for indicating a number of the drug dispensed from the device.

According to an embodiment, the dose button comprises a tubular shape. The dose indicator element may comprise a ring-like shape. The dose indicator element may be permanently or releasably arranged within the tube of the dose button.

During insertion of the dose indication element into the dose button, a force may arise which tends to alter the relative position of the dose button and the dose indication element. The substance which may, for example, be applied to the bearing surface of the dose indication element, may counteract said force, hence, preventing unintentional movement of the dose indication element with respect to the dose button during insertion.

A further aspect relates to a method for assembling a drug delivery device. The drug delivery device comprises a first component. The drug delivery device comprises a second component. In a first step, a substance is applied to at least one of the first component and the second component. The substance may adhesively couple to the respective component, e.g. to a bearing surface of the respective component. In a further step, the second component and the first component are permanently or releasably mounted together. An inner friction of the substance is great enough to releasably, in particular temporarily, fix an axial and/or angular position of the second component and the first component with respect to one another during the mounting. In a third step, a third component of the device is permanently or releasably mounted to the second component. Said mounting may cause an axial and/or rotational force acting on the second component. Relative movement of the first component and the second component during mounting of the third component, in particular arising from said force, may be prevented by means of the substance.

During assembly of the device, the axial and/or rotational position of the second component with respect to the first component may be maintained by means of the substance. The inner friction of the substance had to be overcome by the forces acting onto the first and/or the second component during assembly for initiating relative movement. However, the inner friction may be great enough to compensate said forces, thus preventing unintentional relative movement of the first component and the second component during assembly. This may help to maintain a predetermined position of the first component with respect to the second component with respect to one another, thus increasing dose accuracy of the device.

Of course, features described above in connection with different aspects and embodiments may be combined with each other and with features described below.

Further features, advantages and refinements become apparent from the following description of the exemplary embodiments in connection with the accompanying figures.

BRIEF DESCRIPTION OF THE FIGURES

Like elements, elements of the same kind and substantially equivalent or identically acting elements may be provided with the same reference numerals in the figures.

DETAILED DESCRIPTION

Figure 1:
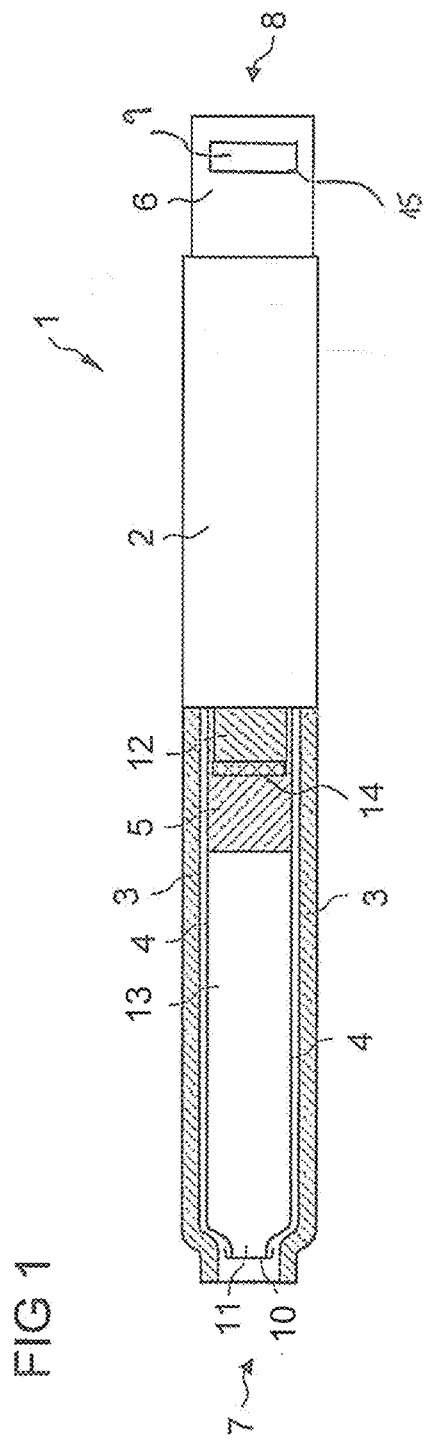
FIG. 1 schematically shows a perspective side view of an exemplary embodiment of a drug delivery device, FIG. 2 schematically shows an embodiment of a dose indication element prior to insertion of the dose indication element, FIG. 3 schematically shows introduction of the dose indicator element of FIG. 2 into a dose button during assembly of the device shown in FIG. 1, FIG. 4 schematically shows the dose indicator element shown in FIG. 2 arranged within the dose button.

In FIG. 1 a drug delivery device 1 is shown. The drug delivery device 1 comprises a housing 2. The drug delivery device 1 and the housing 2 have a distal end 7 and a proximal end 8. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1.

The housing 2 may be designed to enable a safe and comfortable handling of the drug delivery device 1. The housing 2 may be configured to house, fix, protect or guide inner components of the drug delivery device 1, e.g. members of a drive mechanism which is explained later on in more detail. Preferably, the housing 2 limits or prevents the exposure of the inner components to contaminants such as liquid, dirt or dust. The housing 2 may be a unitary or a multipart component. The housing 2 may have a tubular shape, as shown in FIG. 1. Alternatively, the housing 2 may have a non-tubular shape.

The device 1 comprises a cartridge holder 3. The device 1 comprises a cartridge 4. The cartridge 4 is, preferably releasably, secured to the cartridge holder 3. The cartridge holder 3 stabilizes the cartridge 4 mechanically. The cartridge holder 3 and the housing 2 may be, preferably releasably, secured to one another. For this purpose, a proximal end of the cartridge holder 3 may be secured to a distal end of the housing 2, e.g. by means of a bayonet fitting. A cartridge holder 3 which is releasably secured to the housing 2 may be detached from the housing 2, for example in order to allow for introducing a replacement cartridge into the device 1.

The cartridge 4 may hold a plurality of doses of a drug 13. The term "drug" as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy.

In a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The drug delivery device 1 may comprise a needle assembly (not explicitly shown), comprising a needle. The needle assembly may be releasably attached to the cartridge holder 3. Alternatively, the drug delivery device 1 may be a needle-free device.

The cartridge 4 comprises an outlet 11. The outlet 11 may be covered by a membrane 10. The membrane 10 may protect the drug 13 against external influences during storage of the cartridge 4. The cartridge 4 comprises a bung 5. The bung 5 is moveably retained in the cartridge 4. The bung 5 seals the cartridge 4 proximally. Movement of the bung 5 in the distal direction with respect to the cartridge 4 causes the drug 13 to be dispensed from the cartridge 4 through the outlet 11, provided that fluid communication was established between the interior and the exterior of the cartridge 4, e.g. when the membrane 10 is pierced by the needle.

The drug delivery device 1 may be an injection device. The drug delivery device 1 may be a pen-type device, in particular a pen-type injector. The device 1 may be a disposable or a re-usable device. The device 1 may be configured to dispense variable doses, in particular user-settable doses, of the drug 13. Alternatively, the device 1 may be configured to dispense fixed doses of the drug 13, in particular pre-set doses which may not be varied by the user. The drug delivery device 1 may be a manually, in particular a non-electrically, driven device.

The drug delivery device 1 comprises a piston rod 12. The piston rod 12 may be made of a flexible or a rigid material. The piston rod 12 may have a circular or a non-circular cross-section. The piston rod 12 may be a simple rod, a lead-screw, a rack, a pinion system or the like. The piston rod 12 may be of unitary or multipart construction.

The piston rod 12 operates through the housing 2 of the drug delivery device 1. The piston rod 12 is designed to transfer force to the bung 5, thereby driving the bung 5 in the distal direction with respect to the cartridge 4 and the housing 2. In this way, a dose of the drug 13 is dispensed from the cartridge 4 provided that the outlet 11 was opened, e.g. the membrane 10 was pierced by the needle as described above. The size of the dispensed dose is determined by the distance by which the bung 5 is displaced in the distal direction with respect to the housing 2.

A bearing member 14 is arranged between the bung 5 and the piston rod 12 to advance the bung 5. The bearing member 14 is displaceable together with the piston rod 12 with respect to the housing 2. The piston rod 12 is preferably rotatable with respect to the bearing member 14. In this way, the risk that the rotating piston rod 12 drills into the bung 5 and thereby damages the bung 5 is reduced.

The device 1 comprises a drive mechanism. The drive mechanism is configured to drive the piston rod 12. In particular, the drive mechanism is configured for transferring force, preferably user-exerted force, particularly preferably manually exerted force, to the bung 5 by means of the piston rod 12 for displacing the bung 5 with respect to the cartridge 4 in the distal direction. A dose of the drug 13 may be dispensed from the cartridge 4 in this way.

The drive mechanism comprises a dose button 6. The dose button 6 may comprise a tubular shape. The dose button 6 may comprise or may be embodied as a sleeve. The dose button 6 is configured to be gripped by the user. The dose button 6 is moveable with respect to the housing 2. The dose button 6 may be moveable in the proximal direction with respect to the housing 2 for setting a dose of the drug 13. The dose button 6 may be moveable in the distal direction with respect to the housing 2 for delivering the set dose. The distance by which the dose button 6 is displaced with respect to the housing 2 during setting of the dose may determine a size of the dose. The dose button 6 comprises a window 15.

The drive mechanism comprises a dose indication element 9. The dose indication element 9 may comprise a ring-like shape. The dose indication element 9 comprises a size suited for introduction of the dose indication element 9 into the dose button 6 during an assembly of the device 1. Once introduced into the dose button 6, the dose indication element 9 is, at least partly, visible through the window 15. The dose indication element 9 may be at least one of rotatable and axially moveable with respect to the dose button 6 during operation of the device 1, e.g. during setting and/or delivering of a dose of the drug 13.

Figure 2:
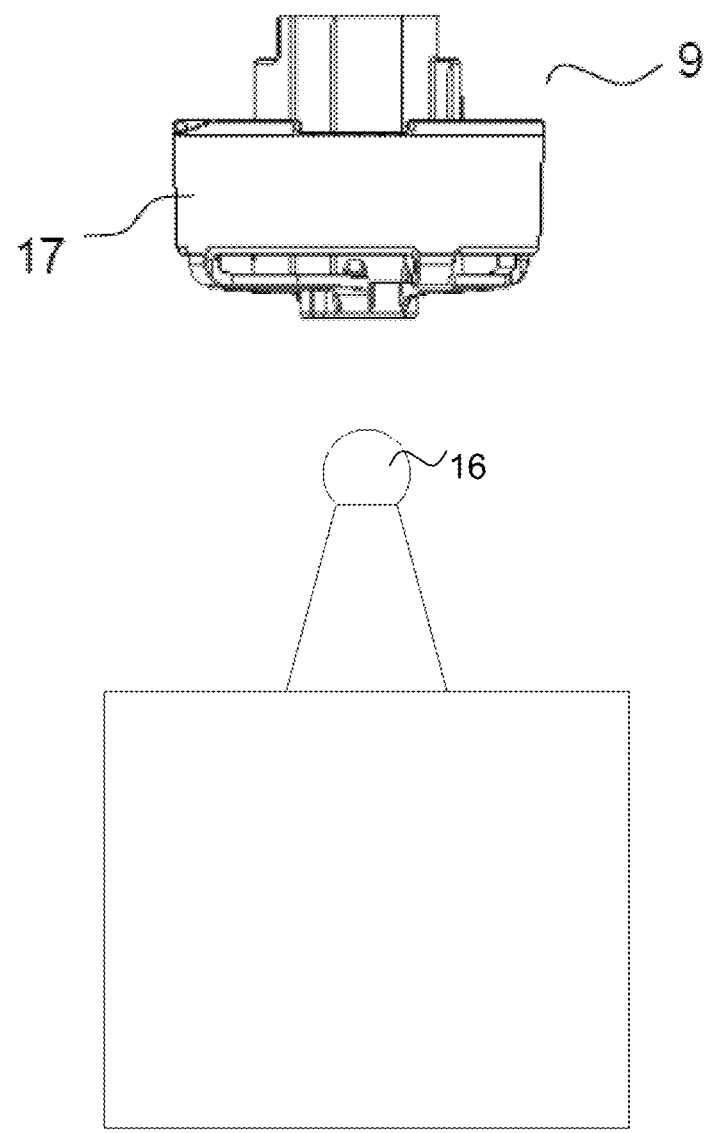

The dose indication element 9 comprises an outer surface, in particular a bearing surface 17 (see FIG. 2). The bearing surface 17 is configured to mechanically cooperate with, in particular to contact, an inner surface, e.g. a bearing surface 18 (see FIG. 4), of the dose button 6 which is explained later on in more detail.

The dose indication element 9 may be configured to display the number of doses of the drug 13 dispensed from the device, for example. Alternatively, the dose indication element 9 may be adapted to indicate at least two different operation conditions of the device 1, e.g. an unprimed condition and a primed condition, of the device 1. When the device 1 is in the primed condition, a priming dose of the drug 13 was dispensed from the device 1.

Unintentional movement, e.g. rotation, of the dose indication element 9 with respect to the dose button 6 may lead to displaying a wrong number of doses dispensed from the device 1 or to displaying a wrong operation condition of the device 1. In the latter case, for example, an unintentionally rotated dose indication element 9 may indicate a primed condition of the device 1, although no priming dose has been dispensed so far. This may have fatal or even lethal consequences for the user. Accordingly, it is crucial to prevent unintentional movement of the dose indication element 9 with respect to the dose button 6, in particular to accurately maintain the rotational position of the dose indication element 9 with respect to the dose button 6.

In this context, unintentional movement may comprise each kind of movement, e.g. rotational and/or axial movement, which is not necessary for the intended operation of the device 1, e.g. for priming the device 1, for setting a dose and/or delivering the set dose from the device 1. For example, unintentional movement may occur while inserting the dose indication element 9 into the dose button 6 during assembly of the device 1. Additionally or alternatively, unintentional movement may arise from manipulation of the device 1 during assembly, e.g. introduction of a further component, e.g. the piston rod 12, into the device 1. Additionally or alternatively, unintentional movement may be possible due to tolerances between the dose indication element 9 and the dose button 6 arising from the assembly of the device 1. Additionally or alternatively, unintentional movement may be possible, during intended operation of the device 1, due to manufacturing tolerances of at least one of the dose indication element 9 and the dose button 6 which may lead to play between the dose indication element 9 and the dose button 6. Additionally or alternatively, unintentional movement may arise from an outer impact and/or by a vibration of the device 1 during intended operation of the device 1.

In order to prevent unintentional movement of the dose indication element 9 with respect to the dose button 6, a substance 16 (see FIG. 2) may be applied to at least one of the dose indication element 9 and the dose button 6, which is explained in connection with FIGS. 2 to 4.

FIG. 2 shows an embodiment of the dose indication element 9 prior to insertion of the dose indication element 9 into the dose button 6.

As shown in FIG. 2, the substance 16 is applied to the bearing surface 17 of the dose indication element 9. Additionally or alternatively, the substance 16 may be applied to the bearing surface 18 of the dose button 6 (not explicitly shown). The substance 16 is adhesively coupled to the bearing surface 17 of the dose indication element 9 and/or the bearing surface 18 of the dose button 6. In particular, mechanical cooperation of the respective bearing surface 17, 18 providing the substance 16 and the other one of the bearing surfaces 17, 18 may not lead to removal of the substance 16.

Figure 3:
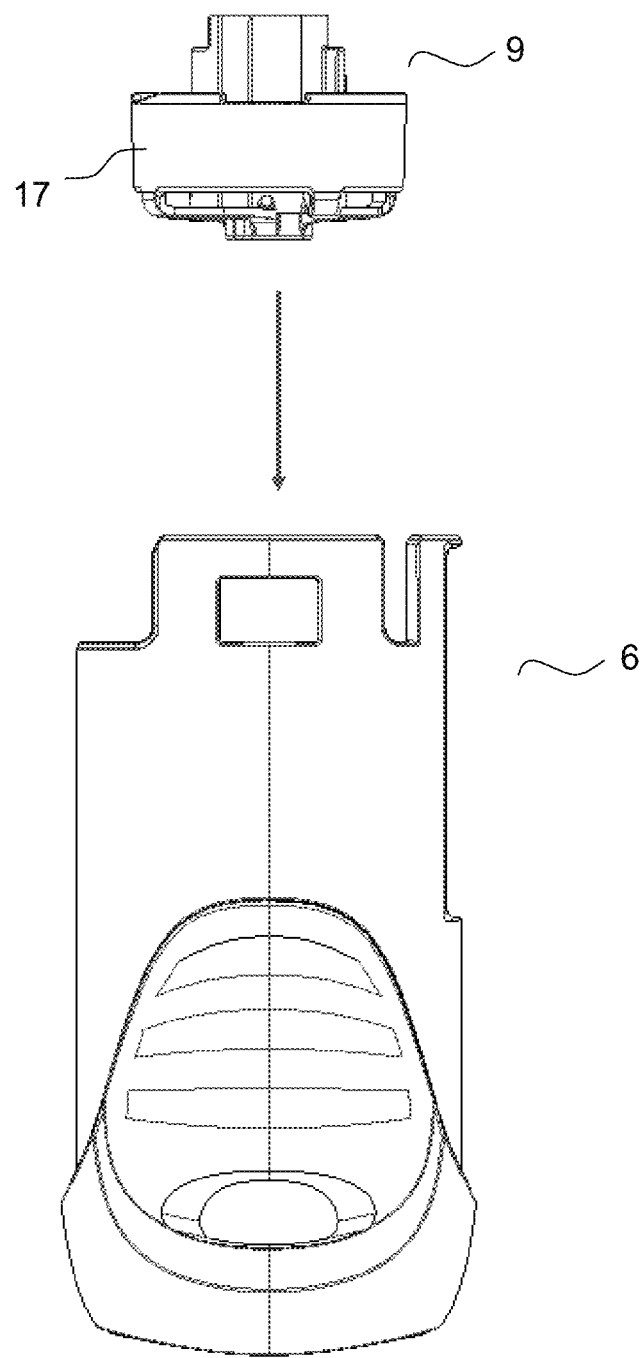

The substance 16 is applied prior to assembly of the device 1 and, in particular, prior to insertion of the dose indication element 9 into the dose button 6 (see FIGS. 3 and 4). Once the dose indication element 9 is inserted into the dose button 6, the bearing surfaces 17, 18 mechanically cooperate, thus bringing the substance 16 into contact with the bearing surface 18 of the dose button 6 (see FIG. 3).

The substance 16 has an inner friction. The inner friction has to be overcome, e.g. by a force exerted by the drive mechanism onto the dose indication element 9 and/or the dose button 6, for achieving relative movement of the dose button 6 and the dose indication element 9. In particular, the inner friction may be such that unintentional relative movement of the dose button 6 and the dose indication element 9, e.g. during assembly, is prevented with relative movement necessary for operation of the device 1 being allowed, which is explained in more detail in connection with FIGS. 3 and 4. The inner friction may comprise a constant value in the range of operating temperatures of the device 1, e.g. in the range of 0° and 40°. The substance 16 may comprise a viscous fluid, e.g. a grease.

FIG. 3 shows the insertion of the dose indication element 9 into the dose button 6 during assembly of the device 1.

After the substance 16 was applied, the dose indication element 9 is inserted into the dose button 6, as shown in FIG. 3. Upon insertion, the bearing surfaces 17, 18 mechanically cooperate with one another. Accordingly, the substance 16 is brought into contact with the respective bearing surface 17, 18. Due to said cooperation, the dose button 6 and the dose indication element 9 are temporarily secured to one another. In particular, the dose button 6 and the dose indication element 9 are secured against unintentional relative movement, e.g. rotation, by means of the substance 16, in particular due to the inner friction of the substance 16. In other words, the applied amount of the substance 16 and/or its inner friction is great enough to stabilize the orientation, in particular the angular position, of the dose indication element 9 with respect to the dose button 6 during insertion of the dose indication element 9 into the dose button 6. The applied amount of the substance 16 and/or its inner friction is great enough to compensate the forces acting on the dose indication element 9 during insertion of the dose indication element 9. In this way, it is guaranteed that the dose indication element 9 is positioned at its predetermined angular position within the dose button 6 after assembly was completed, e.g. the dose indication element 9 may indicate after assembly that zero doses have been dispensed from the device 1 so far.

FIG. 4 shows a part of the device 1 shown in FIG. 1. In particular, FIG. 4 shows a cross-sectional view of the dose button 6 after insertion of the dose indication element 9 into the dose button 6.

After insertion of the dose indication element 9, further components of the device 1 may be assembled, e.g. the piston rod 12 may be introduced into the device 1 (not explicitly shown in FIG. 4). Thereby, the substance 16 applied to the respective bearing surface 17, 18 again prevents rotation of the dose indication element 9 by counteracting the forces acting on the dose indication element 9 when further components are introduced into the device 1. In particular, the applied amount of the substance 16 and/or its inner friction is also great enough to stabilize the orientation, in particular the angular position, of the dose indication element 9 with respect to the dose button 6 during insertion of the further components, e.g. the piston rod 12.

After assembly was completed, the device 1 may be ready for operation. The bearing surfaces 17, 18 are still in mechanical cooperation with one another. Accordingly, the substance 16 is in contact with the respective bearing surface 17, 18. The applied amount of the substance 16 and/or its inner friction is great enough to stabilize the intended angular and/or axial position of the dose indication element 9 with respect to the dose button 6 during the intended operation of the device 1, in particular during operation of the drive mechanism. In this way, unintentional movement of the dose indication element 9 with respect to the dose button 6, e.g. movement arising from forces acting on the dose indication element 9 due to an outer impact as described above, is prevented during operation. However, the applied amount of the substance 16 and/or its inner friction is small enough to allow movement of the dose indication element 9 with respect to the dose button 6 which is necessary during the intended operation of the device 1, e.g. for rotation of the dose indication element 9 for indicating the dispensed number of doses of the drug 13. In particular, a force applied to the dose indication element 9 by means of the drive mechanism during operation of the device 1 is great enough to overcome the inner friction of the substance 16. The inner friction of the substance 16 is small enough such that relative movement of the dose indication element 9 with respect to the dose button 6 during intended operation is enabled without destroying the respective bearing surface 17, 18 or the respective component of the device 1, i.e. the dose indication element 9 or the dose button 6.

As described above, the substance 16 may be applied to the dose indication element 9. However, the substance 16 may be applied to any other component of the device 1, in particular components of the drive mechanism, to be secured against unintentional movement during assembly and intended operation of the device 1. Said components may comprise the piston rod 12, for example.

The outer shape of said components, e.g. of the dose indication element 9, the dose button 6, the piston rod 12, may be determined by the intended operation of the drive mechanism. In particular, the outer shape may not be suited to restrict or even prevent unintentional movement as described above by means of further elements of the device 1, e.g. holding features, mechanically interacting with the respective component.

Other implementations are within the scope of the following claims. Elements of different implementations may be combined to form implementations not specifically described herein.

The invention claimed is:

1. A drug delivery device comprising:
   a housing;
   a cartridge holder connected to the housing;
   a first component and a second component, wherein the first component is axially moveable with respect to the housing during a setting and a dispensing of a dose, wherein the second component can rotate with respect to the first component during the setting and the dispensing of the dose, but is axially fixed with the first component during dose setting, wherein a substance is provided on at least one of the first component and the second component, wherein an inner friction of the substance stabilizes at least one of the orientation and the position of the first component and the second component with respect to one another, and wherein the inner friction of the substance allows relative rotatable movement of the first component and the second component, and wherein a predetermined position of the first and the second component with respect to each other is maintained by the substance,
   wherein the first component comprises a dose button configured as a tube and having a window and is configured to be actuated by a user for at least one of setting and dispensing a dose of a drug from the device, and wherein the second component comprises a dose indication element that is permanently arranged within the tube so that the dose indication element,
   is visible through the window;
   moves axially with the dose button during dose setting; and
   is configured to display a number of doses of a drug dispensed from the device or to display an operation condition of the device.

2. The drug delivery device according to claim 1, wherein the inner friction of the substance prevents relative movement of the first and second component caused by an outer impact or by a vibration of the device.

3. The drug delivery device according to claim 1, wherein the inner friction of the substance prevents relative movement of the first and the second component arising from a manufacturing tolerance of at least one of the first component and the second component and/or during assembly of the device.

4. The drug delivery device according to claim 1, wherein a force applied to at least one of the first component and the second component during intended operation of the device overcomes the inner friction of the substance.

5. The drug delivery device according to claim 1, wherein relative movement between the first component and the second component comprises at least one of relative rotational and axial movement.

6. The drug delivery device according to claim 1, wherein the first component and the second component are part of a drive mechanism of the device, and wherein operation of the drive mechanism causes relative movement of the first and second components.

7. The drug delivery device according to claim 1, wherein an outer shape of the first component and the second component is predetermined for the intended operation of the device.

8. The drug delivery device according to claim 1, wherein the substance is adhesively coupled to a bearing surface of at least one of the first component and the second component.

9. The drug delivery device according to claim 1, wherein the substance comprises a viscous fluid.

10. The drug delivery device according to claim 1, wherein the dose indication element comprises a ring-like shape.

11. A method for assembling a drug delivery device comprising:
    a housing;
    a cartridge holder connected to the housing;
    a first component comprising a dose button having a window and configured as a tube to be actuated by a user for at least one of setting and dispensing a dose of a drug from the device; and a second component axially fixed with the first component during dose setting and comprising a dose indication element that is visible through the window and is permanently arranged within the tube so that the dose indication element,
    is visible through the window;
    moves axially with the dose button during dose setting; and
    is configured to display a number of doses of a drug dispensed from the device or to display an operation condition of the device, the method comprising the steps of:
    applying a substance to at least one of the first component and the second component,
    mounting the second component and the first component together such that the first component is axially moveable with respect to the housing and the second component is rotatable with respect to the first component, wherein an inner friction of the substance releasably fixes a position of the second component and the first component with respect to one another during the mounting, wherein a predetermined position of the first and the second component with respect to each other is maintained by the substance,
    mounting a third component of the device to the second component, where relative movement of the first component and the second component during mounting of the third component is prevented by the substance.

12. The method of claim 11, wherein the inner friction of the substance prevents relative movement of the second component and the first component with respect to one another caused by manipulation of the device during the assembly.

\* \* \* \* \*